(12) United States Patent
Malin et al.

(10) Patent No.: US 6,966,772 B2
(45) Date of Patent: Nov. 22, 2005

(54) METHOD OF ADJUSTING A DRILL BUSHING FOR A DENTAL IMPLANT

(75) Inventors: Leo J. Malin, N3622 Brookview Rd., La Crosse, WI (US) 54601; Robert J. Harter, La Crosse, WI (US)

(73) Assignee: Leo J. Malin, La Crosse, WI (US)

( * ) Notice: Subject to any disclaimer, the term of this patent is extended or adjusted under 35 U.S.C. 154(b) by 153 days.

(21) Appl. No.: 10/429,100

(22) Filed: May 2, 2003

(65) Prior Publication Data

US 2004/0219481 A1 Nov. 4, 2004

(51) Int. Cl.$^7$ .................................................. A61C 3/00
(52) U.S. Cl. ......................................... 433/75; 433/215
(58) Field of Search ............................ 433/75, 74, 173, 433/215, 72, 76

(56) References Cited

U.S. PATENT DOCUMENTS

| | | |
|---|---|---|
| 3,748,739 A | 7/1973 | Thibert |
| 4,998,881 A | 3/1991 | Lauks |
| 5,015,183 A | 5/1991 | Fenick |
| 5,015,186 A | 5/1991 | Detsch |
| 5,064,374 A | 11/1991 | Lundgren |
| 5,133,660 A | 7/1992 | Fenick |
| 5,350,297 A | 9/1994 | Cohen |
| 5,613,852 A | 3/1997 | Bavitz |
| 5,718,579 A | 2/1998 | Kennedy |
| 5,725,376 A * | 3/1998 | Poirier ..................... 433/172 |
| 5,967,777 A * | 10/1999 | Klein et al. ................ 433/75 |
| 6,201,880 B1 * | 3/2001 | Elbaum et al. ............. 382/100 |
| 6,283,753 B1 | 9/2001 | Willoughby |
| 6,319,006 B1 * | 11/2001 | Scherer et al. ............. 433/215 |
| RE37,646 E | 4/2002 | Zuest |
| 6,488,502 B1 | 12/2002 | Weber |
| 2002/0182567 A1 | 12/2002 | Hurson et al. |

FOREIGN PATENT DOCUMENTS

| | | |
|---|---|---|
| EP | 0437031 A1 | 7/1991 |
| WO | WO99/26540 | 6/1999 |

* cited by examiner

Primary Examiner—Melba N. Bumgarner
(74) Attorney, Agent, or Firm—Robert J. Harter

(57) ABSTRACT

A method for a dental implant process involves creating an overall image that shows a trajectory of a drill bushing in relation to a patient's jaw. The overall image shows a trajectory image that represents the trajectory of the drill bushing and a jaw image that represents the jaw. The method allows a user to move the trajectory image relative to the jaw image, which can be useful when adjusting the angular position of the actual drill bushing.

2 Claims, 3 Drawing Sheets

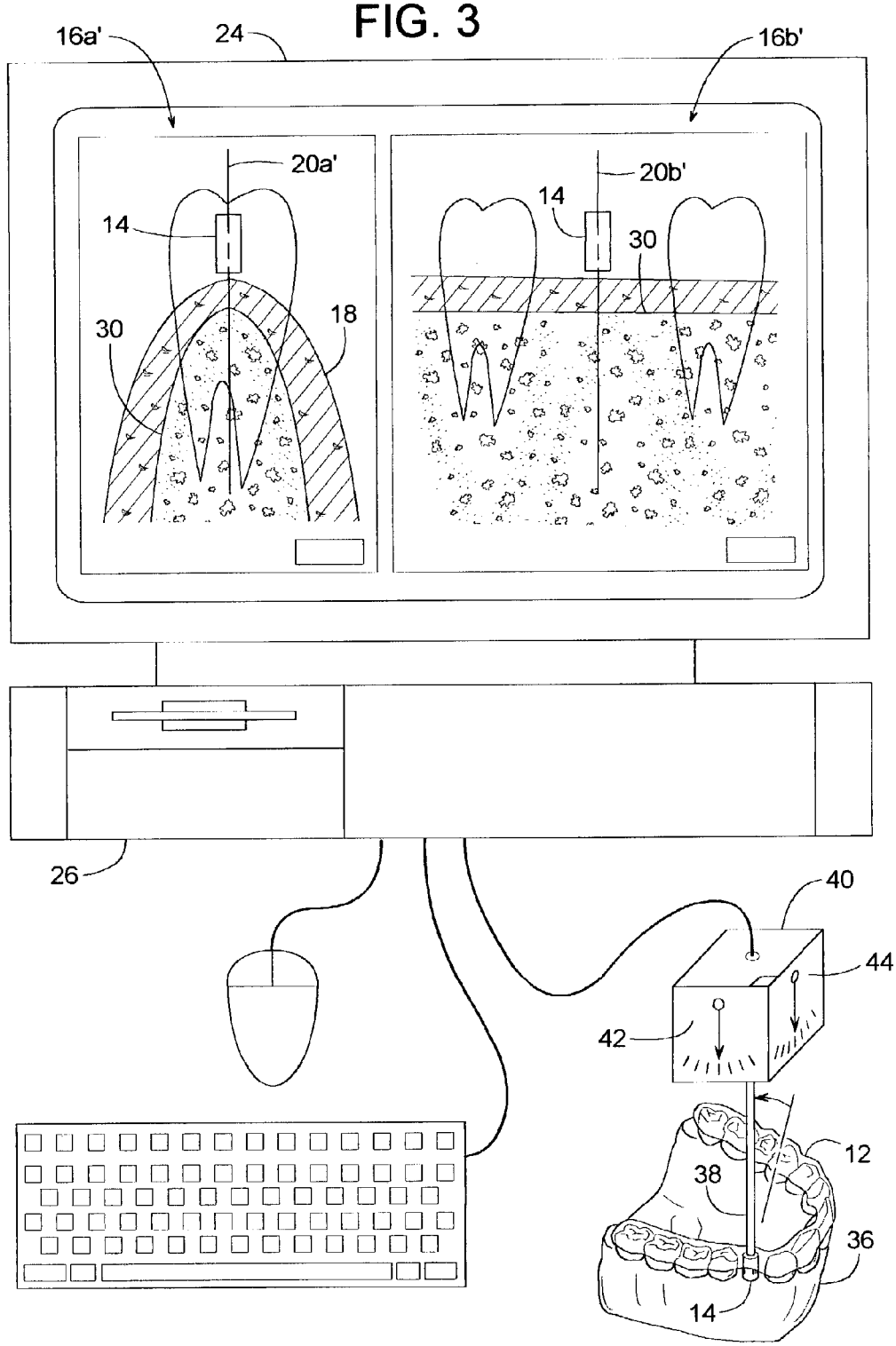

METHOD OF ADJUSTING A DRILL BUSHING FOR A DENTAL IMPLANT

BACKGROUND OF THE INVENTION

1. Field of the Invention

The subject invention generally pertains to dental implants and more specifically to a method for adjusting the position of a drill bushing used for installing the implant.

2. Description of Related Art

Various dental implant methods and devices have been developed for replacing one or more missing teeth in a person's jaw with prosthetic teeth. For many prosthetic teeth, a final product comprises three basic components: an implant, an abutment, and a crown. The crown is the exposed portion of the prosthesis that resembles one or more teeth. The implant is an anchor that becomes attached to the jawbone, and the abutment couples the crown to the implant.

To install the implant, a hole is usually drilled into the patient's jawbone, and the implant is inserted into the hole.

A drill bushing attached to a stent can be used to help guide the drill bit, as disclosed in PCT Publication WO 99/26540 and U.S. Pat. Nos. 5,015,183; 5,133,660; 5,718,579. A drill bushing, unfortunately, can be difficult to align in the proper direction.

Although the image of implants have been tilted, translated and otherwise manipulated with respect to an image of a jawbone, such image manipulations fail to show how the orientation of an existing drill bushing may need to be adjusted to achieve a desired drill trajectory.

Thus, a need exists for a better method of aligning a drill bushing to a patient's jawbone.

SUMMARY OF THE INVENTION

To adjust the angular position of a drill bushing used in a dental implant process, it is an object of some embodiments of the invention to adjust a trajectory image of the drill bushing relative to a jaw image of the patient.

Another object of some embodiments is to allow a user to move the trajectory image relative to the jaw image to determine how far the actual drill bushing may need to be tilted.

Another object of some embodiments is to use a computer mouse to move the trajectory image of the drill bushing.

Another object of some embodiments is to use a computer keyboard to move the trajectory image of the drill bushing.

Another object of some embodiments is to use an electronic inclinometer to move the trajectory image of the drill bushing.

Another object of some embodiments to adjust the position of the trajectory image along two dimensional planes that are at right angles to each other.

Another object of some embodiments is to simultaneously adjust the trajectory image and the actual drill bushing, thereby achieving generally instantaneous feedback.

Another object of some embodiments is to use tomography in creating an overall image that depicts the trajectory image and the jaw image.

One or more of these and other objects of the invention are provided by creating an overall image that shows a trajectory of a drill bushing in relation to a patient's jaw, wherein the overall image shows a trajectory image that represents the trajectory of the drill bushing and a jaw image that represents the jaw; and moving the trajectory image relative to the jaw image.

BRIEF DESCRIPTION OF THE DRAWING

FIG. 3 is a schematic view similar to FIG. 2 but showing two trajectory images at another position.

DESCRIPTION OF THE PREFERRED EMBODIMENT

Figure 1:
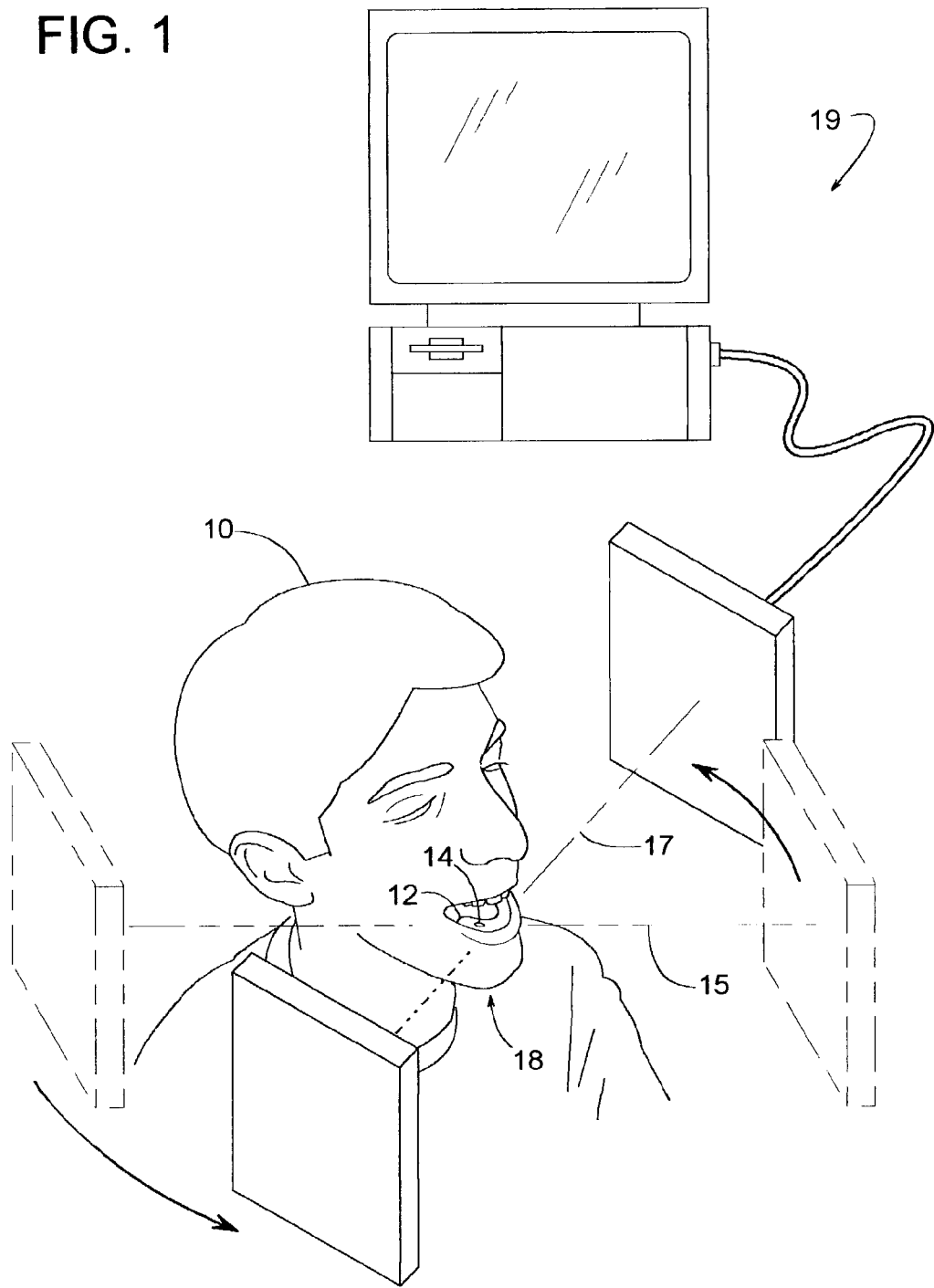
FIG. 1 is a perspective view of a tomograph system being used to help create at least one overall image of a drill bushing in relation to a patient's jaw.

FIG. 1 shows a tomograph or a series of X-rays being taken of a patient 10 that has a surgical dental stent 12 engaging the patient's jaw. The term, "jaw" refers to that part of a patient's body that comprises one or more of the following: teeth, gums, and/or jawbone (upper or lower). Stent 12 is a conventional surgical dental stent that mates with the patient's jaw and can be produced in various ways that are well known to those skilled in the art. A drill bushing 14 is attached to stent 12 in an area of a missing tooth. Bushing 14 can help guide a drill bit in drilling a hole into the patient's jaw. An implant can then be inserted into the hole and anchored to the jaw.

Figure 2:
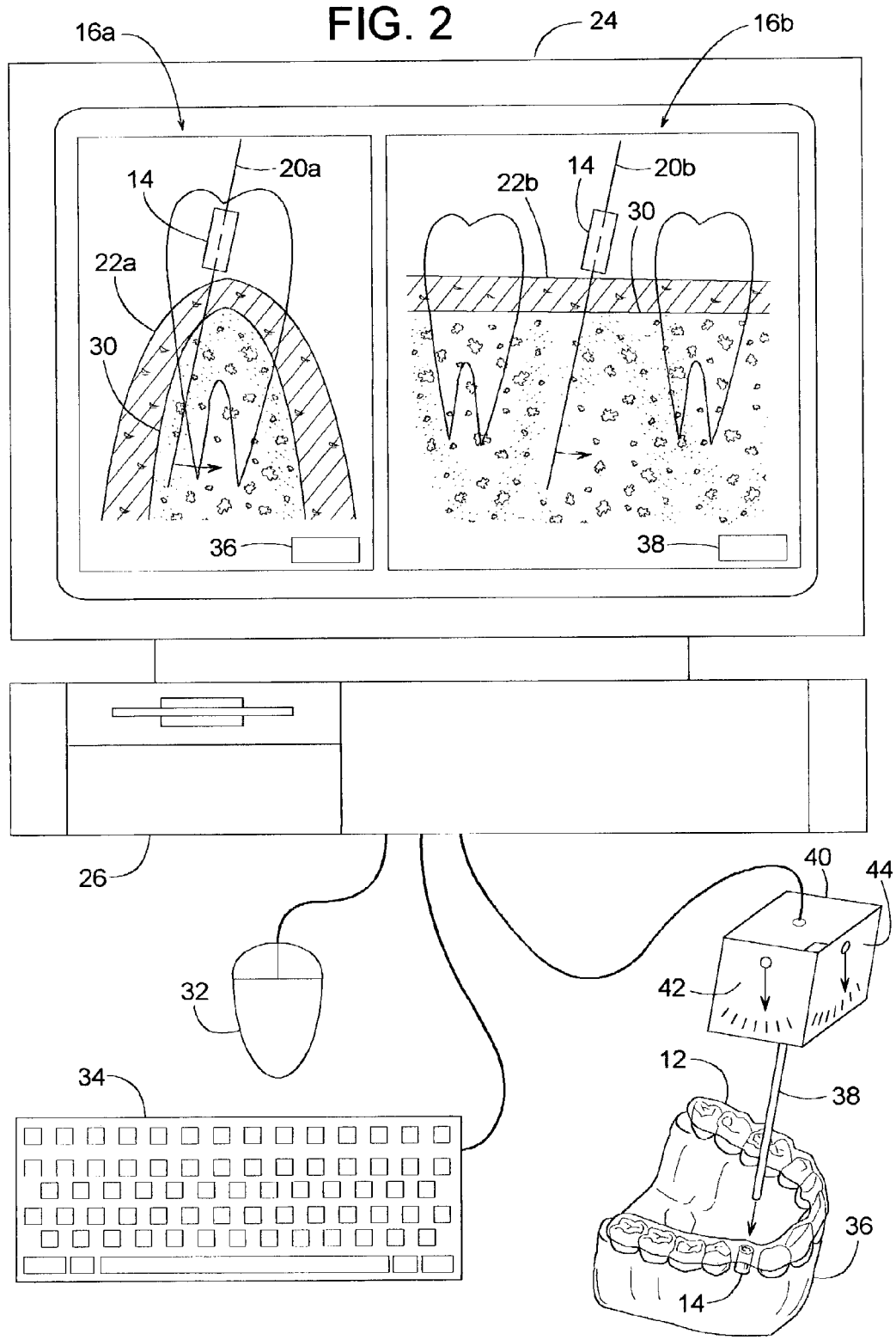
FIG. 2 is a schematic view that illustrates moving a trajectory image relative to a jaw image.

Bushing 14 is preferably made of a material that can be detected by the X-rays, so at least one overall image 16a can be created which shows bushing 14 and/or its trajectory (i.e., the bushing's longitudinal centerline) in relation to the patient's jaw 18 as shown in FIGS. 2 and 3. Overall image 16a, for example, shows a trajectory image 20a and a jaw image 22a that are displayed on a conventional computer monitor 24 controlled by a computer 26. Trajectory image 20a represents the trajectory of bushing 14, and jaw image 22a represents the patient's jaw. In some cases, monitor 24 also displays a second overall image 16b where the first overall image 16a presents a front view of the patient's jaw, and the second overall image 16b is a side view. Thus, the two views 16a and 16b are taken along planes that are intersecting and preferably perpendicular to each other.

The equipment and method for taking a tomographical scan is well known to those skilled in the art. Tomography generally involves creating a computer-generated image from a plurality of X-rays as indicated by lines 15 and 17. Other terms used for tomography include, but are not limited to, CT scan (computed tomographical scan), EIT (electrical impedance tomography), CAT scan (computerized axial tomography). System 19 is schematically illustrated to represent all types tomography systems. Some examples of system 19 include, but are not limited to a CommCAT IS-2000, Panorex CMT, and a Panorex CMT Plus, all of which are products of Imaging Sciences International, Inc., of Hatfield, Pa.

FIG. 2 shows that the trajectory of bushing 14 is not aimed directly into the patient's jawbone 30, so trajectory images 20a and 20b can be moved or tilted to correct the misalignment. Moving trajectory images 20a and 20b can be done in various ways.

In some cases, overall images 16a and 16b are created by importing, "cut-and-pasting," or otherwise incorporating a tomograph into an appropriate software program. One example of such a program includes, but is not limited to, "Micrografx Designer, Technical Edition" by Micrografx, Inc. of Richardson, Tex. Using a standard "click-and-drag" technique, a conventional computer mouse 32 (or keyboard 34, depending on the software) can be used to move or tilt trajectory images 20a and 20b (which can be a centerline drawn using the Micrografx software). An angular displacement or degree to which trajectory images 20a and 20b are tilted can be displayed in areas 36 and 38 and manually recorded for later reference.

Next, stent 12 with bushing 14 can be placed onto a model 36 of the patient's jaw. Model 36 can be cast or otherwise made in a conventional manner well known to those skilled in the art. A tool 38 or lever can be inserted into bushing 14, and tool 38 can then be manually tilted based upon the angular displacement values displayed in areas 36 and 38. The extent to which tool 38 tilts bushing 14 can be measured using a clinometer 40 (electronic or otherwise) that is mounted to or otherwise associated with tool 38. The term, "clinometer" refers to any tool for measuring a change in inclination.

In some cases, clinometer 40 comprises two electronic levels 42 and 44 that are perpendicular to each other. The angle readings from levels 42 and 44 can be communicated to computer 26 so that trajectory images 20a and 20b tilt in response to tilting tool 38. The angle reading from level 42 tilts trajectory image 20b, and the angle reading from level 44 tilts trajectory image 20a. In effect, tool 38 functions as a joystick with trajectory images 20a and 20b following the joystick's movements. The joystick inserted into bushing 14 can be tilted in various directions and angles until trajectory images 20a' and 20b' point directly into jawbone 30 as shown by images 16a' and 16b' of FIG. 3. Electronic levels 42 and 44 can be any inclination measuring instrument that provides an electronic signal whose value (analog or digital) can be inputted into a computer using a conventional appropriate I/O board or module.

Once drill bushing 14 is properly aimed, bushing 14 can be permanently affixed to stent 12 using a conventional bonding material. Stent 12 can then be returned to the patient's mouth where bushing 14 can help guide the drill bit in drilling the implant hole in the patient's jawbone.

Although the invention is described with reference to a preferred embodiment, it should be appreciated by those skilled in the art that various modifications are well within the scope of the invention. Therefore, the scope of the invention is to be determined by reference to the following claims.

What is claimed is:

1. A method for adjusting a drill bushing used for installing a dental implant in a jaw of a patient, the method comprising:
    creating an overall image that shows a trajectory of a drill bushing in relation to the jaw, wherein the overall image shows a trajectory image that represents the trajectory of the drill bushing and a jaw image that represents the jaw;
    using a computer to display the overall image on a computer monitor;
    tilting the drill bushing with a tool that indicates a change in angular position of the drill bushing, wherein the tool is in communication with the computer,
    in response to tilting the drill bushing with the tool, moving the trajectory image relative to the jaw image.

2. The method of claim 1 wherein the overall image is created with the use of tomography.

* * * * *